US010495445B2

(12) United States Patent
Kress et al.

(10) Patent No.: US 10,495,445 B2
(45) Date of Patent: Dec. 3, 2019

(54) GLASS CONTAINER INSPECTION SYSTEM

(71) Applicant: Applied Vision Corporation, Cuyahoga Falls, OH (US)

(72) Inventors: Michael Leo Kress, Uniontown, OH (US); Amir Novini, Akron, OH (US); Richard A. Sones, Cleveland Heights, OH (US); Kellen Reusser, Wooster, OH (US)

(73) Assignee: Applied Vision Corporation, Cuyahoga Falls, OH (US)

( * ) Notice: Subject to any disclaimer, the term of this patent is extended or adjusted under 35 U.S.C. 154(b) by 0 days.

(21) Appl. No.: 15/855,934

(22) Filed: Dec. 27, 2017

(65) Prior Publication Data

US 2019/0195619 A1   Jun. 27, 2019

(51) Int. Cl.
*G01B 11/06* (2006.01)

(52) U.S. Cl.
CPC .................. *G01B 11/06* (2013.01)

(58) Field of Classification Search
CPC .... G01B 11/06; G01B 11/0691; G01B 21/085
See application file for complete search history.

(56) References Cited

U.S. PATENT DOCUMENTS

| 4,553,217 A | 11/1985 | Daudt et al. |
| 5,583,337 A | 12/1996 | Chan |
| 5,834,661 A | 11/1998 | Nonaka et al. |
| 6,188,079 B1* | 2/2001 | Juvinall ................ G01B 11/06 250/223 B |
| 6,840,666 B2 | 1/2005 | Enachescu et al. |
| 6,863,860 B1* | 3/2005 | Birckbichler .......... B29C 49/78 250/341.8 |
| 9,803,974 B2 | 10/2017 | Bathelet |

(Continued)

FOREIGN PATENT DOCUMENTS

WO     2011137264 A1    11/2011

OTHER PUBLICATIONS

"IR lenses maximize detector potential" May 1, 2005, Vision Systems Design, available at: https://www.vision-systems.com/articles/print/volume-10/issue-5/features/product-focus/ir-lenses-maximize-detector-potential.html to Wilson (Year: 2005).*

(Continued)

*Primary Examiner* — Kenneth J Malkowski
(74) *Attorney, Agent, or Firm* — Medley, Behrens & Lewis, LLC (57) ABSTRACT

Described herein are various technologies pertaining to determining whether at least a portion of a sidewall of a glass container has insufficient thickness. A glass container inspection system comprises an infrared camera in communication with a computing system. The infrared camera is configured to capture an infrared image of an exterior of the sidewall of the glass container at long-wavelength infrared as the glass container undergoes a temperature change. The computing system receives the infrared image from the infrared camera and outputs an indication that at least the portion of the sidewall of the glass container has insufficient thickness based on the infrared image. The indication may also be based on a statistical model derived from infrared images of glass containers having sidewalls of known sufficient thickness.

20 Claims, 8 Drawing Sheets

(56) References Cited

U.S. PATENT DOCUMENTS

| | | |
|---|---|---|
| 2006/0049352 A1 | 3/2006 | Irani |
| 2008/0291438 A1 | 11/2008 | Akkerman et al. |
| 2009/0278286 A1* | 11/2009 | Schmidt ................ G01B 11/06 |
| | | 264/408 |
| 2013/0162986 A1 | 6/2013 | Kibat et al. |
| 2014/0174127 A1 | 6/2014 | Dalstra |
| 2015/0076353 A1* | 3/2015 | Bathelet ................ B07C 5/3408 |
| | | 250/340 |
| 2015/0142163 A1 | 5/2015 | Simon |
| 2015/0276380 A1 | 10/2015 | Leconte |
| 2017/0322018 A1* | 11/2017 | Hanan ................ G01B 11/0691 |

OTHER PUBLICATIONS

"International Search Report and Written Opinion for PCT Patent Application No. PCT/US18/67201", dated Mar. 8, 2019, 9 pages.

* cited by examiner

GLASS CONTAINER INSPECTION SYSTEM

BACKGROUND

During manufacture of a glass container, defects may be introduced into one or more sidewalls of the glass container. An exemplary defect in glass containers is insufficient sidewall thickness. A glass container with insufficient sidewall thickness may be at risk to break when it is populated with content, especially when the content is a liquid that is sprayed into the glass container at a high velocity.

When a glass container breaks due to insufficient sidewall thickness, a production and/or filling line may be required to be shut down while the broken glass container is cleaned up, thus leading to decreased glass container production and/or filling. There are several approaches for testing glass containers for insufficient sidewall thickness. A first exemplary approach uses a capacitive sensor system. In this approach, electrodes are placed in physical contact with the exterior of the sidewall of the container, and a value that is indicative of capacitance of a region of the glass corresponding to where the electrodes are in contact with the exterior of the sidewall is obtained. The value can be used to derive a thickness of the sidewall at the region of the glass. The container can then be rotated while the electrodes remain in contact with the sidewall of the container, such that thickness of the glass container can be ascertained for a cross-section of the container. This approach is not practical for testing the thickness of the entirety of the glass container, as the measurement only tests the thickness through a plane that extends through the glass container. Additionally, this approach requires physical contact of the electrodes with the glass container and rotation of the glass container, which is disadvantageous as it may interfere with glass container production and/or filling.

A second exemplary conventional approach utilizes a laser. The laser is configured to emit a laser beam at an acute angle relative to the exterior of the sidewall of the glass container. When the laser beam reaches the sidewall, part of the laser beam reflects off the exterior surface of the sidewall and another part of the laser beam reflects off the interior surface of the sidewall. An optical sensor captures these two reflections, and a distance between the captured reflections can be used to determine thickness of the sidewall at the point on the sidewall where the laser impinges upon the sidewall. While this approach does not require physical contact (such as in the first approach), it can only test sidewall thickness at specific points along the sidewalls of the glass container. Like the approach described above, the number of points on the sidewalls of the glass container for which thickness values can be obtained can be increased by rotating the container while the laser beam is directed towards the container. Requiring that the glass container be rotated to inspect thickness may interfere with production and filling of glass containers.

Another exemplary conventional approach for determining thickness at points along a sidewall of glass container includes the use of a chromatic confocal sensor to ascertain thickness at individual points along the sidewall; this approach has deficiencies similar to the deficiencies of the approaches described above, in that measurements are limited to single points, and to acquire additional measurements involves rotating the glass container. Moreover, for each of the approaches referenced above, the sensors must either be in close proximity to or in contact with the sidewall of the glass container while the glass container is being rotated; accordingly, the conventional approaches referenced above are limited to measuring thickness of cylindrical glass containers, and are ill-suited for measuring thickness of non-round glass containers.

Yet another conventional approach utilizes a short-wavelength infrared camera (i.e., a camera configured to detect radiation having wavelengths between 1.4-3 μm). After a glass container has been produced and while the glass container is still hot, the container is placed in a brick oven. Responsive to the glass container being uniformly heated, the glass container will radiate energy. The thicker the sidewall of the glass container, the more energy that will be radiated from the sidewall. The infrared camera captures an image of short-wavelength infrared radiation being irradiated from the container. A thickness of a point on the sidewall captured in the image is ascertained utilizing any suitable approach, and a thickness distribution over a region of the sidewall of the glass container is computed based upon intensity values of the image and the ascertained thickness at the point on the sidewall. While this approach can test sidewall thickness along a region of the sidewall (unlike the approaches described above), it requires that the glass container be heated to a high temperature in order for the camera to be able to capture short-wavelength infrared radiation being radiated from the glass container. Additionally, glass is transparent to short-wavelength infrared radiation. Thus, the image generated by the camera may include unwanted artifacts in the form of infrared radiation being irradiated from an opposite side of the glass container, which can lead to an incorrect thickness assessment.

SUMMARY

The following is a brief summary of subject matter that is described in greater detail herein. This summary is not intended to be limiting as to the scope of the claims.

Described herein is a glass container inspection system that is configured to ascertain whether a sidewall of a glass container has insufficient thickness. More specifically, described herein is a glass container inspection system that comprises a camera that detects mid to long-wave infrared radiation (e.g., infrared radiation having a wavelength of 3 to 12 μm), wherein the camera is configured to generate an infrared image of an exterior of the sidewall of the glass container, and further where a determination is made as to whether the sidewall of the glass container has sufficient thickness based upon the infrared image.

With more specificity, as noted above, the infrared camera is configured to capture an infrared image of an exterior of a sidewall of a glass container as the exterior of the sidewall is undergoing a temperature change. Glass is opaque to radiation at mid to long-wavelength infrared, meaning that radiation at such wavelengths does not propagate through the sidewall of the glass container. Thus, the radiation captured in the infrared image is emitted from the exterior of the sidewall (and not, for example, from the sidewall on the opposite side of the glass container). Each pixel in the infrared image has an intensity value that is indicative of a temperature at a point on the exterior of the sidewall that is captured in the pixel. Thinner portions of the sidewall undergo a temperature change more rapidly than thicker portions of the sidewall. Thus, in an example, when the sidewall is heated and subsequently exposed to a cooler temperature, a thinner portion of the sidewall radiates heat more quickly than a thicker portion of the sidewall, and thus will have a lower surface temperature for a short time after being exposed to the cooler temperature when compared to a surface temperature of the thicker portion. Hence, pixels in the infrared image corresponding to the thinner portions of the sidewall will have lesser intensity than pixels in the infrared image corresponding to thicker portions of the sidewall.

The glass container inspection system further includes a computing system in communication with the infrared camera. After the infrared camera has captured the infrared image of the exterior of the sidewall, the computing system can receive the image from the infrared camera. The computing system can then output an indication that at least a portion of the sidewall of the glass container has insufficient thickness based on the image. For instance, the computing system can perform a comparison between each pixel in the infrared image and a corresponding statistic in a statistical model derived from infrared images of glass containers having sidewalls of known sufficient thickness. The computing system can then output the indication based on the comparison.

The technologies described herein exhibit numerous advantages over conventional glass container inspection systems. First, the glass container inspection system described herein can determine whether a sidewall of a glass container has insufficient thickness at temperatures near room temperature, if desired (as opposed to the third conventional approach described above). Second, the glass container inspection system can determine whether the entire sidewall of the glass container is of sufficient thickness, as opposed to just a few points along the sidewall. Third, the glass container inspection system can be used with glass containers that are non-round and/or asymmetric (while still being suitable for use with round and symmetric containers). Fourth, the glass container inspection system can inspect glass containers more accurately than conventional technologies, as glass is opaque to mid to long-wavelength infrared radiation, and hence an infrared image generated by an infrared camera that is configured to detect mid to long wavelength infrared radiation will fail to capture radiation emitted from the opposite side of the container.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to detecting insufficient thickness of sidewalls of a glass container are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Further, as used herein, the term "exemplary" is intended to mean serving as an illustration or example of something, and is not intended to indicate a preference.

Moreover, as used herein, the terms "component" and "system" are intended to encompass instructions stored in computer-readable data storage that are configured to cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

As used herein, the term "container" refers to a hollow three-dimensional object with a sidewall, a bottom, and at least one opening through which content may be deposited into the container. After content has been deposited into the container, the container may then be sealed using a sealing means. For instance, the sealing means may be a cap, a plug, or a lid. The sealing means need not be made of the same material as the container. A container may have uniform or nonuniform shape (e.g., non-symmetric). A "glass container" refers to a container made of glass. In a non-limiting example, a glass container may be a bottle, a jug, a jar, a cylinder, a bucket, a box, etc. A glass container may be clear or may be tinted with a color.

Described herein are features pertaining to a glass container inspection system that utilizes an infrared camera that is configured to detect mid to long-wavelength infrared radiation (e.g., 3 to 12 μm) emitted from an exterior of a sidewall of a glass container and generate an image based upon such infrared radiation. For example, the mid to long-wavelength infrared radiation detected by the infrared camera can be from 7 to 12 µm, from 7.5 to 11.5 µm, from 8 to 10 µm, or from 9 to 9.5 µm. Glass is opaque to mid to long-wavelength infrared; thus, the infrared camera detects radiation emitted from the exterior of the sidewall (and not, for instance, from an interior of the sidewall or from an opposite side of the container). The intensity of each pixel in the infrared image is representative of a temperature at a point on the exterior of the sidewall represented by the pixel. The glass container inspection system can utilize the infrared image in conjunction with a statistical model in order to identify whether the sidewall (or portions of the sidewall) are of insufficient thickness.

Figure 1:
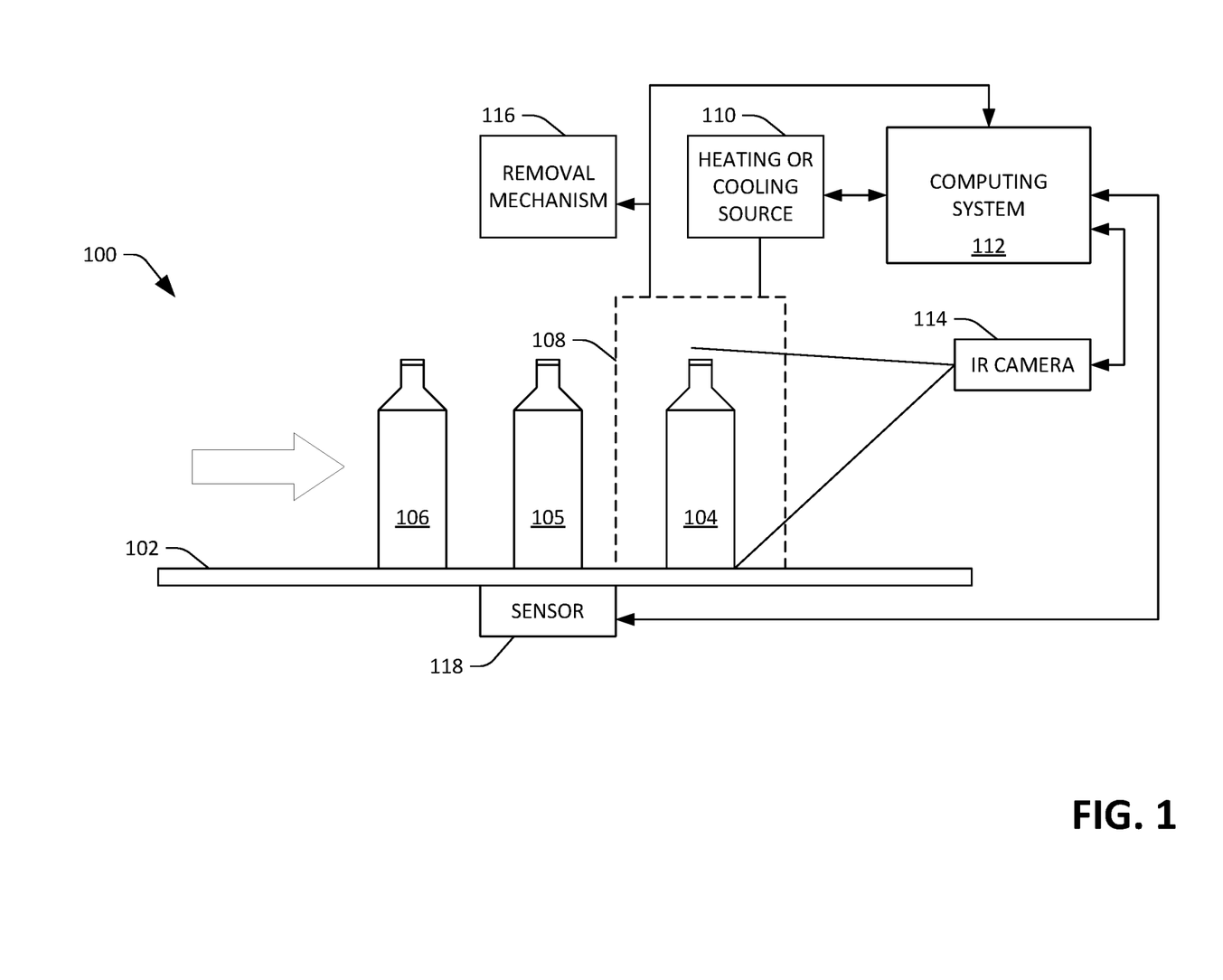
FIG. 1 is a functional block diagram of an exemplary glass container inspection system.

With reference now to FIG. 1, an exemplary glass container inspection system 100 is illustrated. For example, the glass container inspection system 100 can be used to identify portions of a sidewall of a glass container that have an insufficient thickness.

A conveyor 102 transports a plurality of glass containers 104-106 through an inspection area 108. In an embodiment, the inspection area 108 can be located proximate a hot end of a glass container manufacturing process, such that the plurality of glass containers 104-106 are still hot (e.g., hundreds of degrees C.) when each of the containers 104-106 reach the inspection area 108. In another embodiment, the inspection area 108 can be configured to receive the containers 104-106 when such containers 104-106 are at or near room temperature.

The exemplary glass container inspection system 100 may further include a sensor 118 that outputs a signal to the computing system 112 that is indicative of when a glass container (e.g., the glass container 104) has entered the inspection area 108. For example, and not by way of limitation, the sensor 118 may be a presence detector that can detect when the glass container 104 has passed a particular point. In another example, the sensor 118 may be a rotary sensor that is configured to output data based upon movement of the conveyor 102. Thus, this data is indicative of a position of the glass container 104 relative to a previous position of the glass container 104 on the conveyor 102, and therefore the position of the glass container 104 relative to the inspection area 108.

The glass container inspection system 100 may also optionally include a heating or cooling source 110 that is configured to cause the glass container 104 to undergo a temperature change within the inspection area 108 or prior to reaching the inspection area 108. For instance, the heating or cooling source 110 can cause the glass container 104 to undergo a temperature change plus or minus 10 degrees relative to a starting temperature of the glass container 104. In an embodiment where the glass container inspection system 100 is located immediately after a hot end of a glass container manufacturing process, the heating or cooling source 110 may not be necessary, as the natural cooling of the glass container may be sufficient to cause the temperature change.

The glass container inspection system 100 includes an infrared camera 114 that is configured to capture an infrared image of an exterior of a sidewall of the glass container 104, wherein the infrared camera 114 is configured to detect mid to long-wavelength infrared radiation (e.g., wavelengths of 3 to 12 µm). In an embodiment, the infrared camera may comprise a germanium lens. The infrared camera 114 detects mid to long-wavelength infrared radiation emitted from an exterior of the sidewall of the glass container 104 as the glass container 104 undergoes a temperature change. As mentioned previously, glass is opaque to mid to long-wavelength infrared, and hence the infrared image will not capture radiation emitted from an opposite side of the glass container 104 from the side being imaged.

The intensity of the mid to long-wavelength infrared radiation being emitted from a point on the sidewall of the glass container 104 is indicative of a temperature of the exterior of the sidewall at that point. As mentioned above, thinner portions of the glass container 104 will undergo a temperature change faster than thicker portions of the glass container 104. Therefore, for example, when the glass container 104 has a temperature that is greater than that of its surroundings, thinner portions of the glass container 104 will cool more quickly than thicker portions of the glass, and therefore surface temperature at the thinner portions will be lower than surface temperature at the thicker portions. Accordingly, in the infrared image captured by the infrared camera 104, a pixel in the image that corresponds to a thinner portion of the sidewall will have an intensity value that is lower than an intensity value of a pixel in the image that corresponds to a thicker portion of the sidewall. In another example, when the heating or cooling source 110 cools the glass container 104 and the glass container 104 is subsequently heated by ambient air, the thinner portions of the glass container 104 will heat more quickly than the thicker portions of the glass container 104. Thus, while the glass container 104 is warming, the infrared camera 114 captures an infrared image of the container 104, where portions of the infrared image that represent thinner portions of the sidewall have higher intensity than portions of the infrared image that represent thicker portions of the sidewall.

The glass container inspection system 100 further includes a computing system 112 that may be in (wired or wireless) communication with the sensor 118, the infrared camera 114, and the heating or cooling source 110. The computing system 112 can receive a signal from the sensor 118 indicating that the glass container is in the inspection area 108. Responsive to receiving the signal, the computing system 112 can optionally transmit a signal to the heating or cooling source 110, causing the heating or cooling source 110 to either heat or cool the glass container 104. In another example, the heating or cooling source 110 can be operating continuously such that glass containers are heated or cooled as they pass the heating or cooling source 110 along the conveyor 102. While the glass container 104 is undergoing a temperature change (e.g., while the glass container 104 is being heated or cooled by the heating or cooling source 110 or while temperature of the glass container 104 is returning to the ambient temperature after being heated or cooled by the heating or cooling source 110), the infrared camera 114 can capture an infrared image of the glass container 104.

As discussed previously, for example, when the glass container 104 is accepting heat, pixels in the infrared image that are of greater intensity correspond to portions of the sidewall of the glass container 104 that are thinner as compared to other portions of the sidewall of the glass container 104. The computing system 112 can receive the infrared image from the infrared camera 114 and can determine whether any portion of the sidewall of the glass container 104 lacks sufficient thickness based upon the image. When the computing system determines that any portion of the sidewall of the glass container 104 lacks sufficient thickness (e.g., has a region that is thinner than desired), the computing system 112 can output an indication that at least a portion of the sidewall of the glass container 104 has insufficient thickness.

More specifically, the computing system 112 can compare the infrared image with a previously generated (statistical) model of a glass container having the same general shape as the glass container 104. When the infrared image favorably compares with the model, the computing system 112 can deem that the sidewall of the glass container has a suitable thickness across the entirety of the sidewall of the glass container 104. Contrarily, when the infrared image does not favorably compare with the model, the computing system 112 can output an indication that the sidewall of the glass container 104 has at least one region of insufficient thickness. Therefore, in an example, the computing system 112 need not determine actual thickness of the sidewall across the surface of the sidewall; instead, the computing system 112 can determine whether a portion of the sidewall lacks sufficient thickness by comparing the infrared image with the model.

In an embodiment, the glass container inspection system 100 may also include a removal mechanism 116 in communication with the computing system 112. The removal mechanism 116 is generally configured to remove glass containers having insufficient sidewall thickness from the conveyor 102. In an example, the removal mechanism 116 may be a robotic arm controlled by the computing system 112 that can remove the glass container 104 from the conveyor 102 responsive to the computing system 112 outputting an indication that a sidewall of the glass container 104 has insufficient thickness. In another example, the removal mechanism 116 may be a metal block attached to a metal pole controlled by the computing system 112. The computing system 112 can cause the metal pole to push the glass container 104 with insufficient thickness off the conveyor 102 into a waste receptacle responsive to the computing system 112 outputting the indication that the glass container 104 has insufficient thickness.

In another exemplary embodiment, two infrared images of the sidewall of the glass container 104 can be captured as the glass container 104 undergoes a temperature change, and the two infrared images can be compared with one another to ascertain whether the sidewall of the glass container 104 has sufficient thickness (in the portion of the sidewall captured in the images) based upon such comparison. In such an embodiment, the infrared camera 114 can capture both images at different times (e.g., the camera 114 is positioned far enough away from the glass container 104 as the conveyor 102 transports the glass container 104 so that the camera 114 can capture two separate images of the glass container 104 while the glass container 104 is undergoing a temperature change). In another example, the infrared camera 114 can capture a first image and a second infrared camera (not shown) can capture a second infrared image. As described above, when the glass container 104 undergoes a temperature change, thinner portions of the sidewall of the glass container 104 will heat or cool more quickly than thicker portions of the sidewall. Accordingly, differences in intensities between two infrared images of the sidewall of the glass container 104, where the two infrared images are captured at different times as the glass container 104 changes temperature, is indicative of thickness of the sidewall of the glass container 104. Hence, this approach is similar to the one described above (where the computing system 112 compares the infrared image generated by the infrared camera 114 with a model), except that in this embodiment the first infrared image acts as the baseline (model).

In addition, the computing system 112 can be configured to correlate determinations as to whether glass containers have sufficient thickness with molds used to construct the glass containers. With more specificity, in glass production, several molds are employed to generate glass containers simultaneously. Accordingly, the computing system 112 can output indications as to whether the sidewall of the glass container 104 has sufficient thickness based upon both the infrared image generated by the infrared camera 114 and the mold employed to form the glass container 104. In other words, the computing system 112 may have a respective model for each mold stored therein, and can compare the infrared image of the sidewall of the glass container 104 with the model for the mold used to form the glass container 104. In another example, the computing system 112, for each inspected glass container, can generate feedback based upon the mold that generated the glass container; thus, over time, the computing system 112 can identify one or more molds that tend to produce glass containers having sidewalls of insufficient thickness.

For purposes of explanation, the physical theory behind the technologies described herein is now set forth. By way of example, glass containers of mass M and heat capacity $c_p$ moving along the conveyor 102 at frequency f can be considered. Furthermore, the heating or cooling source 110 may be a heat source that delivers energy to each glass container to raise its temperature by $\Delta T$. The average power which must be produced by the heat source 110 is as follows:

$$P = \frac{Mc_p f \Delta T}{\eta} \tag{1}$$

In equation (1), $\eta$ is the fraction of energy absorbed by the glass. As the energy applied by the heat source 110 is applied to the exterior of the sidewall of the glass container 104, it will take a finite amount of time for energy to diffuse through the sidewall. The approximate time is as follows:

$$t_{dif} \sim \frac{0.14 d^2}{\alpha} \tag{2}$$

In equation (2), d is the sidewall thickness and $\alpha$ is the thermal diffusivity of the glass. In order for the temperature of the exterior of the sidewall of the glass container 104 to encode information about the sidewall thickness, an infrared image must be captured at a time at least $t_{dif}$ after the heat source applied heat to the glass container.

In an example, a density $\rho$, heat capacity $c_p$, and thermal conductivity k of a glass container are:

$$\rho \approx 2500 \text{ kg m}^{-3} \tag{3}$$

$$c_p \approx 800 \text{ J kg}^{-1} \text{ K}^{-1} \tag{4}$$

$$k \approx 0.8 \text{ J m}^{-1} \text{ s}^{-1} \text{ K}^{-1} \tag{5}$$

The thermal diffusivity $\alpha$ is then:

$$\alpha = \frac{k}{\rho c_p} \cong 4 \times 10^{-7} \text{ m}^2 \text{s}^{-1} \tag{6}$$

Thus, in an example, for a large glass container (e.g., a glass jug) with mass M=1 kg, conveyor rate f=2 Hz (120 containers per minute), a sidewall thickness of d=2 mm, a temperature change of $\Delta T$=10 K, and $\eta$=0.1 (e.g., from forced air heating), using equations (1) and (2), P=160 kW and $t_{dif}$=1.4 s. In another example, for a smaller glass container (e.g., a glass bottle) with mass M=0.2 kg, conveyor rate f=10 Hz (600 containers per minute), a sidewall thickness of d=1.4 mm, a temperature change of ΔT=10K, and η=0.1, using equations (1) and (2) again, P=160 kW and $t_{dif}$=0.7 s.

In an example, a sidewall of the glass container 104 can be located in an xy plane with z(x, y) denoting a thickness of the sidewall at location (x, y). The sidewall may be imaged with a mid to long-wavelength infrared camera (e.g., the camera 114) with an optical axis along z and T(u, v, t) may denote an absolute temperature on the exterior of the sidewall at a location represented by pixel (u, v) of an infrared image captured by the infrared camera 114 at time t. Thus, the heating energy at the location on the sidewall corresponding to pixel (u, v) at time t, where ρ is the density of the sidewall of the glass container 104, $c_p$ is the heat capacity of the glass, p is the pixel size, and m is the optical magnification is as follows:

$$H(u, v, t) = \frac{\rho c_p p^2}{m^2} z(u, v) T(u, v, t) \tag{7}$$

The temperature distribution T(u, v, t) may change over time due to heat conductance within the sidewall, as well as radiative, conductive, and convective heat transfer to or from the ambient environment. The change of a heat distribution H(u, v, t) is given by equation (8) below, where k is the thermal conductivity of the glass, σ is a constant that governs the energy transferred to the environment by radiation, conduction, and convection, and $T_a$ is the ambient absolute temperature.

$$\delta_t H = kz\nabla^2 T - \frac{\sigma p^2}{m^2}(T - T_a) \tag{8}$$

$\nabla^2 T$ is given by:

$$\nabla^2 T = \delta_u^2 T + \delta_v^2 T \tag{9}$$

Combining equations (7), (8), and (9) results in the following:

$$\delta_t T = \alpha \nabla^2 T - \frac{\beta}{z}(T - T_a) \tag{10}$$

In equation (10), α, the thermal diffusivity of the glass (referenced to the pixel coordinate system) is given by equation (11) and β, an empirical constant depending on the emissivity of the sidewall surface and air flow is given by equation (12).

$$\alpha = \left(\frac{k}{\rho c_p}\right)\left(\frac{m^2}{p^2}\right) \tag{11}$$

$$\beta = \frac{\sigma}{\rho c_p} \tag{12}$$

When equation (10) is solved for z, the following is obtained:

$$Z = \frac{\beta(T - T_a)}{\alpha \nabla^2 T - \delta_t T} \tag{13}$$

The pixel values τ(u, v, t) produced by the infrared camera 114 are linearly related to absolute temperature, where a and b are constants.

$$T(u,v,t) = a + b\tau(u,v,t) \tag{14}$$

Further, $$T - T_a = b(\tau - \tau_a) \tag{15}$$

$$\nabla^2 T = b\nabla^2 \tau \tag{16}$$

$$\delta_t T = b\delta_t \tau \tag{17}$$

Using equations 15-17, equation (13) can thus be represented as follows:

$$Z = \frac{\beta(\tau - \tau_a)}{\alpha \nabla^2 \tau - \delta_t \tau} \tag{18}$$

Therefore, a single infrared image of the sidewall gives the distribution τ(u, v, t) and enables an estimation of the spatial derivatives:

$$\nabla^2 \tau(u,v,t) \cong \tau(u+1,v,t) + \tau(u-1,v,t) + \tau(u,v+1,t) + \tau(u,v-1,t) - 4\tau(u,v,t) \tag{19}$$

If a second infrared image is captured a short time interval Δt after the first infrared image, the time derivative can be estimated as follows:

$$\delta_t \tau(u, v, t) \cong \frac{\tau(u, v, t + \Delta t) - \tau(u, v, t)}{\Delta t} \tag{20}$$

Thus, if the ambient temperature $\tau_a$ and the constants α and β are known, and there are two infrared images τ(u, v, t) and τ(u, v, t+Δt), equations (18), (19), and (20) can be used to estimate the glass thickness distribution z(u, v).

An example is now set forth where the sidewall of the glass container 104 has a known uniform thickness Z. An infrared image of the sidewall may be captured at ambient temperature to obtain $\tau_a$. The center of the sidewall may then be heated to give a non-uniform temperature distribution, and two images τ(u, v, t) and τ(u, v, t+Δt) may then be captured. Equations (19) and (20) may then be used to estimate $\nabla^2\tau(u, v, t)$ and $\delta_t\tau(u, v, t)$. As the sidewall has uniform thickness, equation (14) can be rewritten as follows:

$$Y(u,v,t) = \alpha X(u,v,t) + \gamma \tag{21}$$

In equation (21), X(u, v, t) and Y(u, v, t) are given by equations (22) and (23), respectively (below). Furthermore, α and γ are constants, and γ is given by equation (24).

$$X(u, v, t) = \frac{\nabla^2 \tau}{\tau - \tau_a} \tag{22}$$

$$Y(u, v, t) = \frac{\delta_t \tau}{\tau - \tau_a} \tag{23}$$

$$\gamma = -\frac{\beta}{Z} \tag{24}$$

Y(u, v, t) may then be plotted against X(u, v, t) for all pixels in the heated sidewall. The plot is a straight line with slope α and Y intercept γ. Furthermore, α and γ (and, hence, β) can be estimated from a linear regression and can be used to calibrate the glass container inspection system 100.

Figure 2:
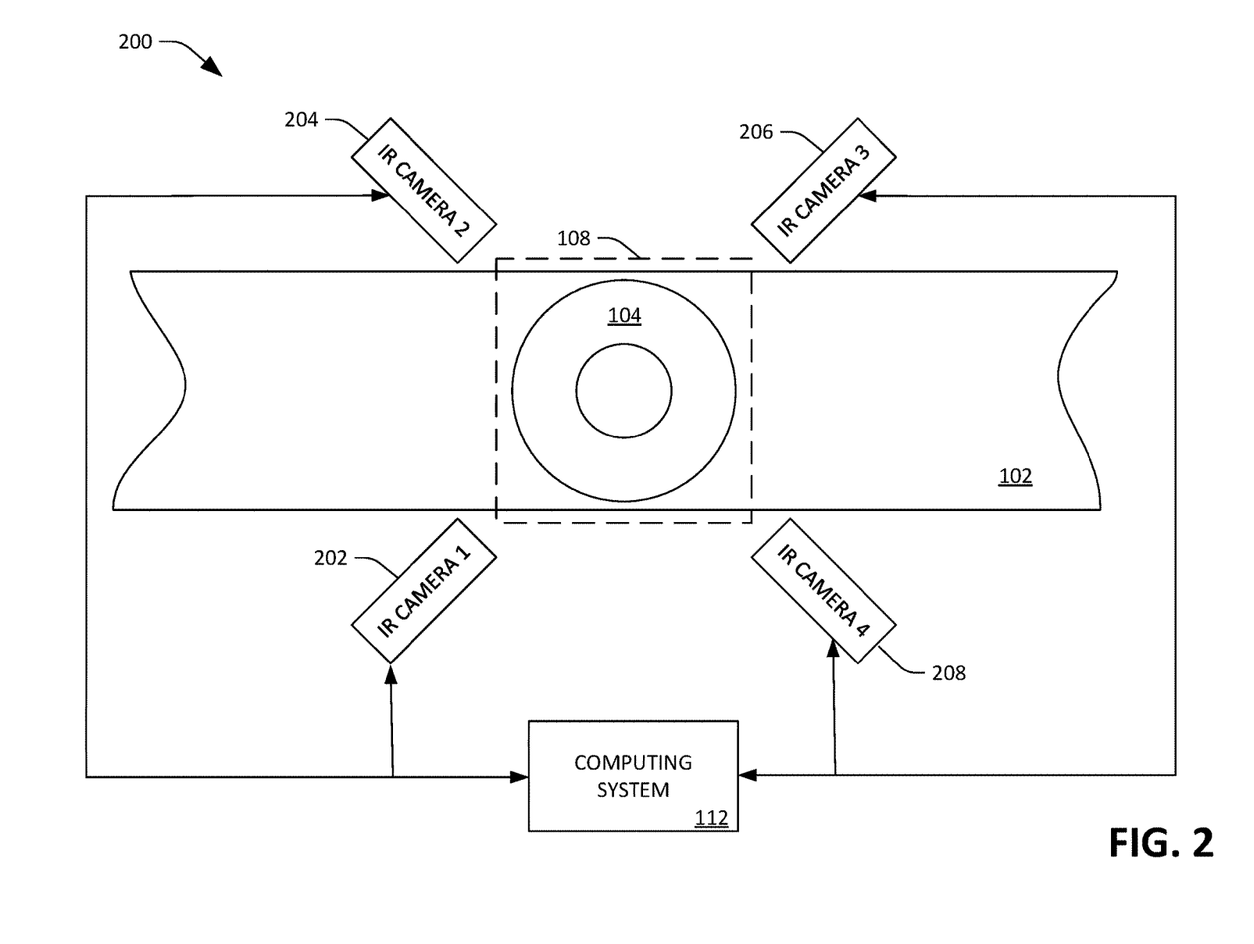
FIG. 2 is an overhead view of an exemplary glass container inspection system including four infrared cameras.

With reference to FIG. 2, an overhead view of another exemplary glass container inspection system 200 is illustrated. As with the system 100, the conveyor 102 transports glass containers through the inspection area 108. In the glass container inspection system 200, a plurality of infrared cameras 202-208 are positioned around the inspection area 108 so as to capture images of the exterior of the sidewall of the glass container 104 that enters the inspection area 108, where the images encompass the entirety of the sidewall of the glass container 104. While the infrared cameras 202-208 are illustrated as being arranged symmetrically around the inspection area 108, other possibilities are contemplated. For instance, when the glass container 104 has a non-uniform shape, the infrared cameras 202-208 can be positioned around the inspection region as a function of the shape of the glass containers. Moreover, the infrared cameras 202-208 may be placed at different elevations from one another with respect to a reference plane (e.g., the plane of the conveyor 102).

Each of the infrared cameras 202-208 can capture an infrared image of the exterior of the sidewall of the glass container 104. For instance, the first infrared camera 202 can capture an infrared image of an exterior of the sidewall of the glass container 104 from a first perspective, the second infrared camera 204 can capture an infrared image of the exterior of the sidewall of the glass container 104 from a second perspective, etc. Moreover, it is understood that the infrared cameras 202-208 can capture infrared images of sidewalls of different geometry on the glass container 104. Collectively, infrared images captured by the infrared cameras 202-208 when the glass container 104 is in the inspection area 108 depict an entirety of the exterior of the sidewall(s) of the glass container 104. While the glass container inspection system 200 is illustrated as including four infrared cameras, it is understood that the glass container inspection system 200 may include more or fewer cameras.

Figure 3:
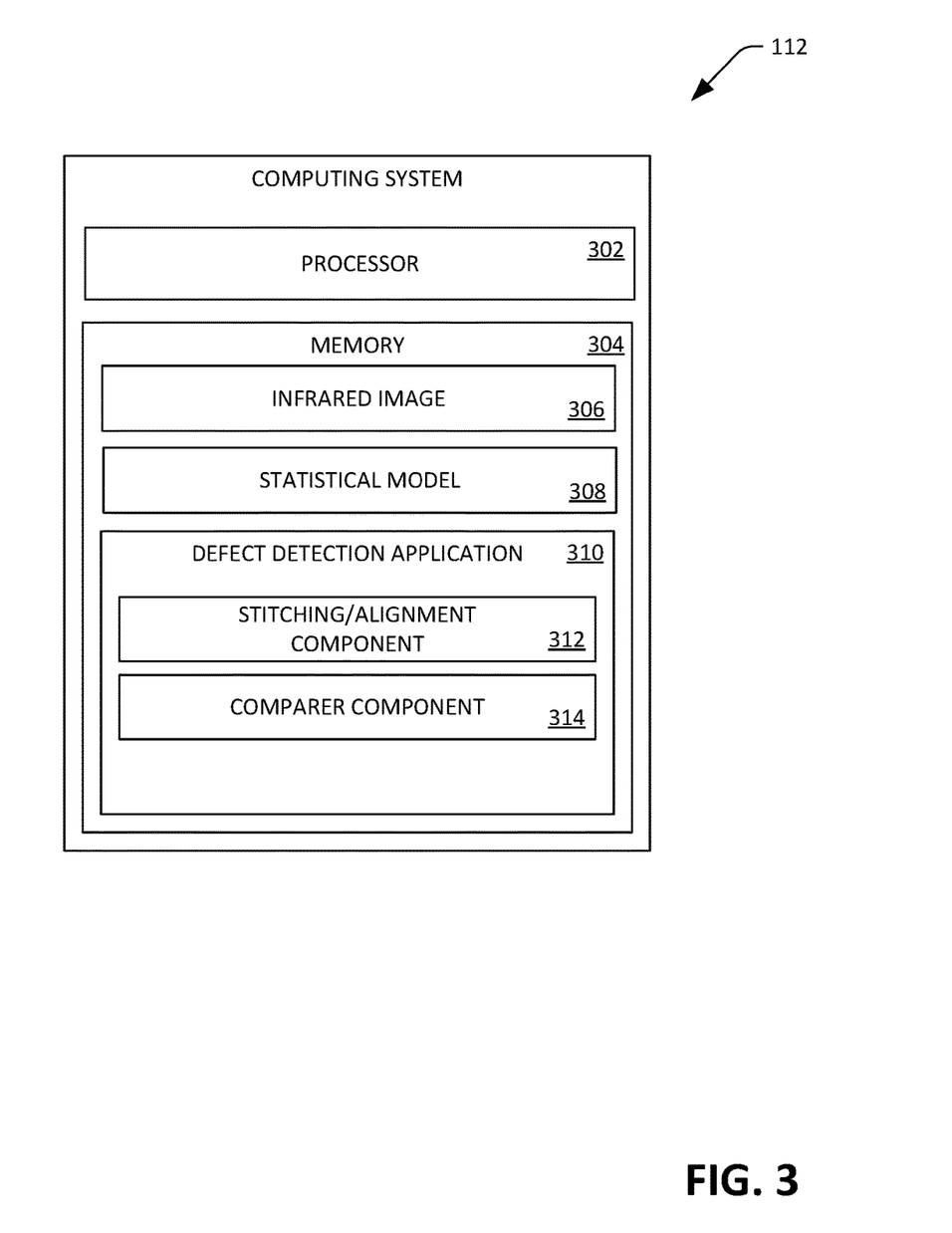
FIG. 3 is a functional block diagram of an exemplary computing system that is configured to determine whether a sidewall of a glass container has insufficient thickness at any location thereof.

Referring now to FIG. 3, a functional block diagram of the computing system 112 is illustrated. The computing system 112 includes a processor 302 and memory 304. The memory 304 has an infrared image 306 (generated by the infrared camera 114) loaded therein. The infrared image 306 is generated by the infrared camera 114, which is configured to detect mid to long-wavelength infrared radiation. While the memory 304 is described as comprising a single infrared image, it is understood that the memory 304 may comprise a plurality of infrared images for a glass container, wherein infrared images are generated by infrared cameras positioned at different positions relative to the glass container 104.

The memory 304 may also have a (statistical) model 308 of a glass container included therein, where the model 308 represents a glass container with sufficient thickness throughout its sidewalls. For instance, the model 308 can comprise a plurality of pixels, and each pixel can have a statistical distribution assigned thereto, where the statistical distribution is indicative of values of the pixel that correspond to a glass container having sidewalls of sufficient thickness. The model 308 can be generated based upon infrared images of glass containers labeled as having sidewalls with sufficient thickness throughout.

With more specificity, the infrared camera 114 (and optionally other infrared cameras) captures infrared images of non-defective glass containers as such containers pass through the inspection area 108. For each non-defective glass container, the computing system 112 "flattens" the images of the exterior(s) of the sidewall(s) of the container such that the entirety of the exterior of the glass container is represented in a two-dimensional grid ("flattened image"). The computing system 112 then aligns each of these flattened images. During alignment, the computing system 112 can perform a suitable image processing technique to create a pixel-by-pixel correspondence between the flattened images, where each pixel has a value assigned thereto, with the value being indicative of an intensity of the pixel. Using these pixel values, the computing system 112 can form the model 308, where the model 308 includes, for instance, a distribution of values for each pixel. While the memory 304 has been described as including a single model, it is understood that the computing system 112 may comprise a plurality of statistical models, wherein the statistical models represent glass containers of different shapes.

The memory 304 additionally has a defect detection application 310 loaded therein. The defect detection application 310 is generally configured to ascertain whether the sidewall of the glass container 104 has insufficient thickness based upon the infrared image 306 and the model 308. The defect detection application 310 includes a stitching/alignment component 312 that is configured to "flatten" infrared images of sidewall(s) of the glass container 104 and stitch the images into a two-dimensional representation of the exterior of the sidewall(s) of the glass container 104.

The defect detection application 310 also includes a comparer component 314 configured to compare the stitched, flattened image with the model 308. The comparer component 314 can perform a comparison between each pixel of the stitched, flattened image and a statistical distribution for each pixel in the model 308, and the comparer component 314 can output an indication that the sidewall of the glass container 104 has sufficient thickness based on the comparison. For instance, if values of the pixels in the stitched, flattened image correspond to statistics in the model 308, the comparer component 314 can output an indication that the glass container 104 is not defective. Contrarily, if values of the pixels of the stitched, flattened image do not correspond to statistics in the model 308, the comparer component 314 can output a signal that the container is defective.

Figure 4:
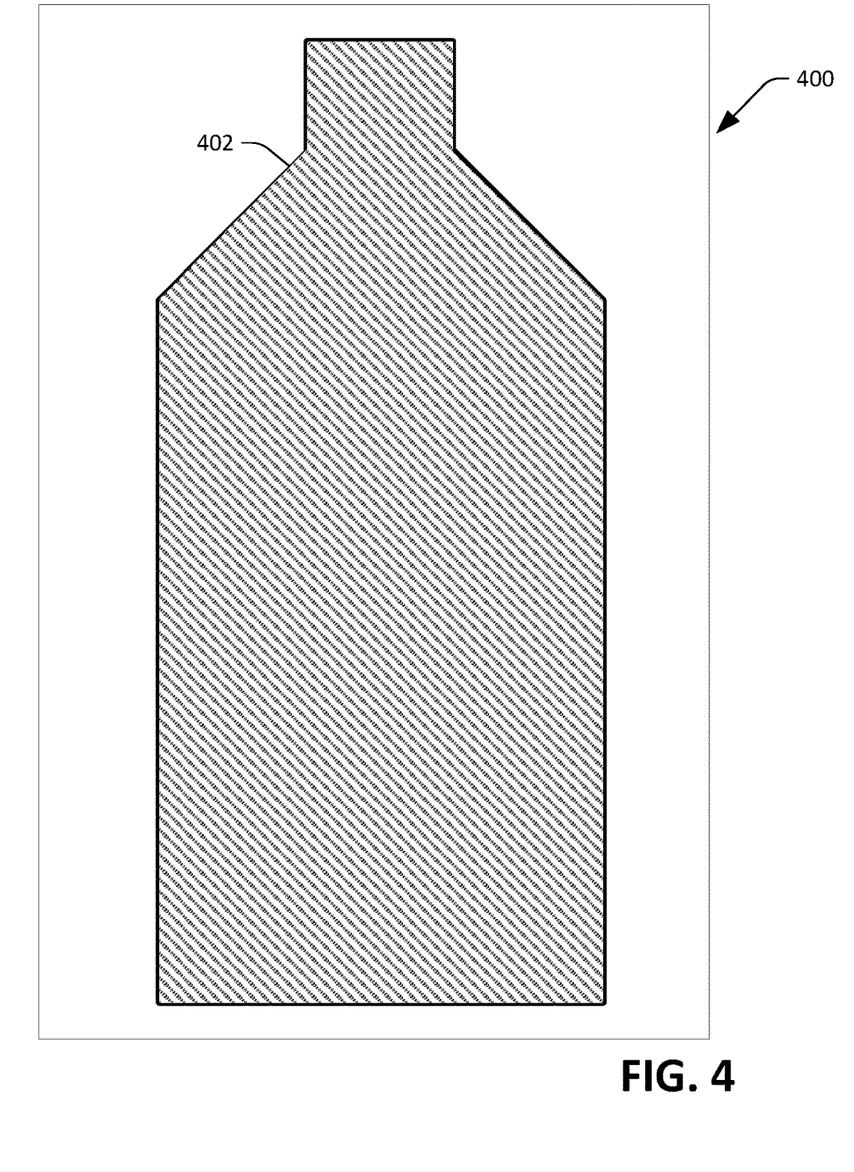
FIG. 4 depicts an exemplary infrared image of an exterior of a sidewall of a glass container.

With reference now to FIG. 4, an exemplary infrared image 400 captured by the infrared camera 114 is illustrated. The infrared image 400 is of a glass container 402. In this example, the entirety of the exterior of the sidewall of the glass container 402 shown in the infrared image 400 is of uniform thickness (indicated by diagonal lines). Furthermore, the sidewall of the glass container 402 shown in the infrared image 400 is of sufficient thickness. Thus, the computing system 112 will identify the glass container 402 as having a sidewall of sufficient thickness based on the infrared image 400.

Figure 5:
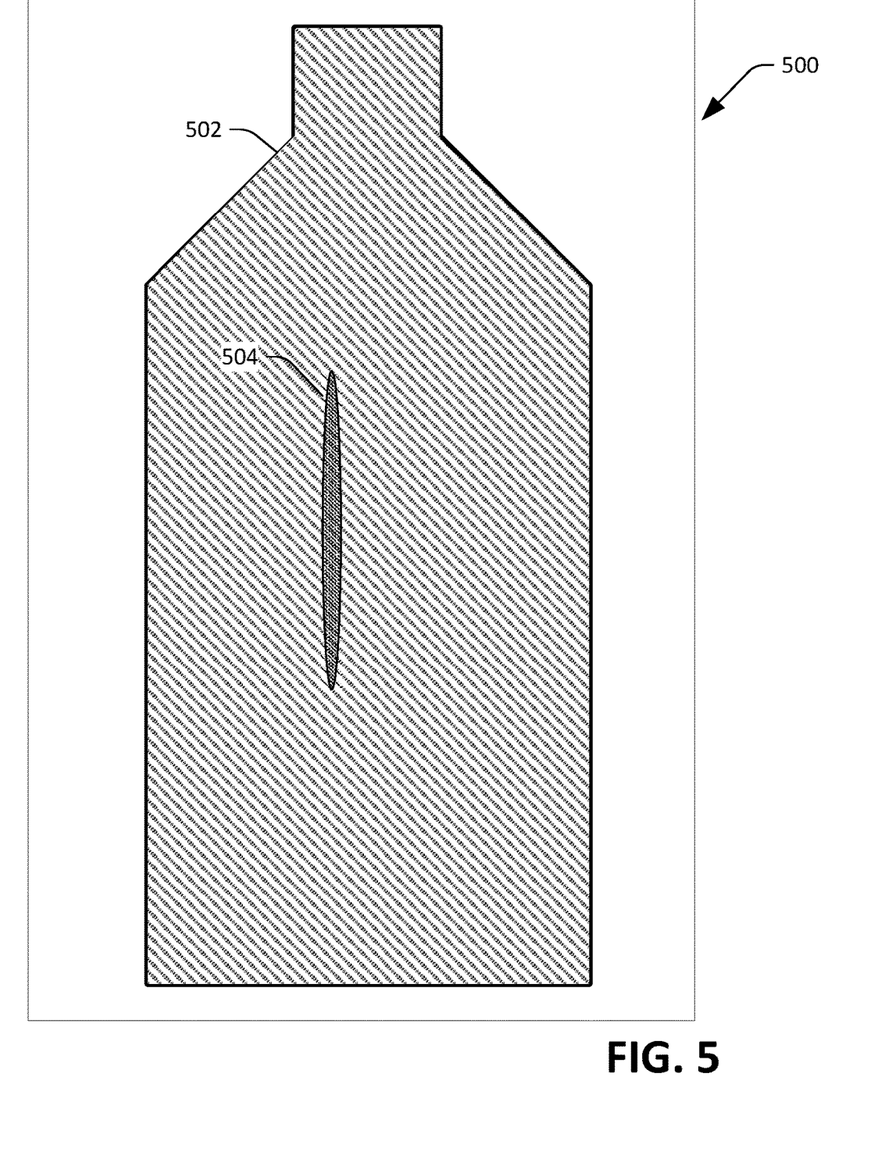
FIG. 5 depicts an exemplary infrared image of an exterior of a sidewall of a glass container that has a portion with insufficient thickness.

Turning now to FIG. 5, another exemplary infrared image 500 captured by the infrared camera 114 is illustrated. The infrared image 500 includes a glass container 502. In this example, a sidewall of the glass container 502 includes a portion 504 of insufficient thickness. As the portion 504 has insufficient thickness, it is depicted in the infrared image 500 as darker than the rest of the glass container 502 (illustrated by dots in the portion 504). The rest of the glass container 502 is of sufficient thickness (illustrated by diagonal lines across the glass container 502). Thus, the computing system 112 can identify the glass container 502 as having a sidewall of insufficient thickness based on the infrared image 500.

As noted previously, the infrared camera 114 can comprise a lens that includes germanium. The transmission window of germanium (where transmission percentage is at its peak) is between about 2.5-12 μm at 25 C, rendering germanium particularly well-suited for detecting infrared radiation in wavelengths where types of glass of interest are opaque. For example, the transmission window for soda lime at 1 mm thickness includes wavelengths from about 0.25-3 μm, and soda lime at such thickness is opaque at wavelengths above about 3 μm. The transmission window for sapphire, at 1 mm thickness, is between about 0.1 and 7 μm. The transmission windows for UV grade fused silica at 5 mm thick, semiconductor grade fused quartz at 5 mm thick, and borosilicate at 1 mm thick are all below 5 μm. Accordingly, the types of glass referenced above are all opaque at mid to long wavelength, while the infrared camera 114, when incorporating a germanium lens, is able to resolve minor temperature differences across an exterior surface of a sidewall of a glass container (due to the percentage of transmission being relatively flat for mid to long-wavelength infrared radiation), and hence the glass container inspection system 100 is able to accurately identify portions of insufficient thickness on the sidewalls of glass containers.

Figure 6:
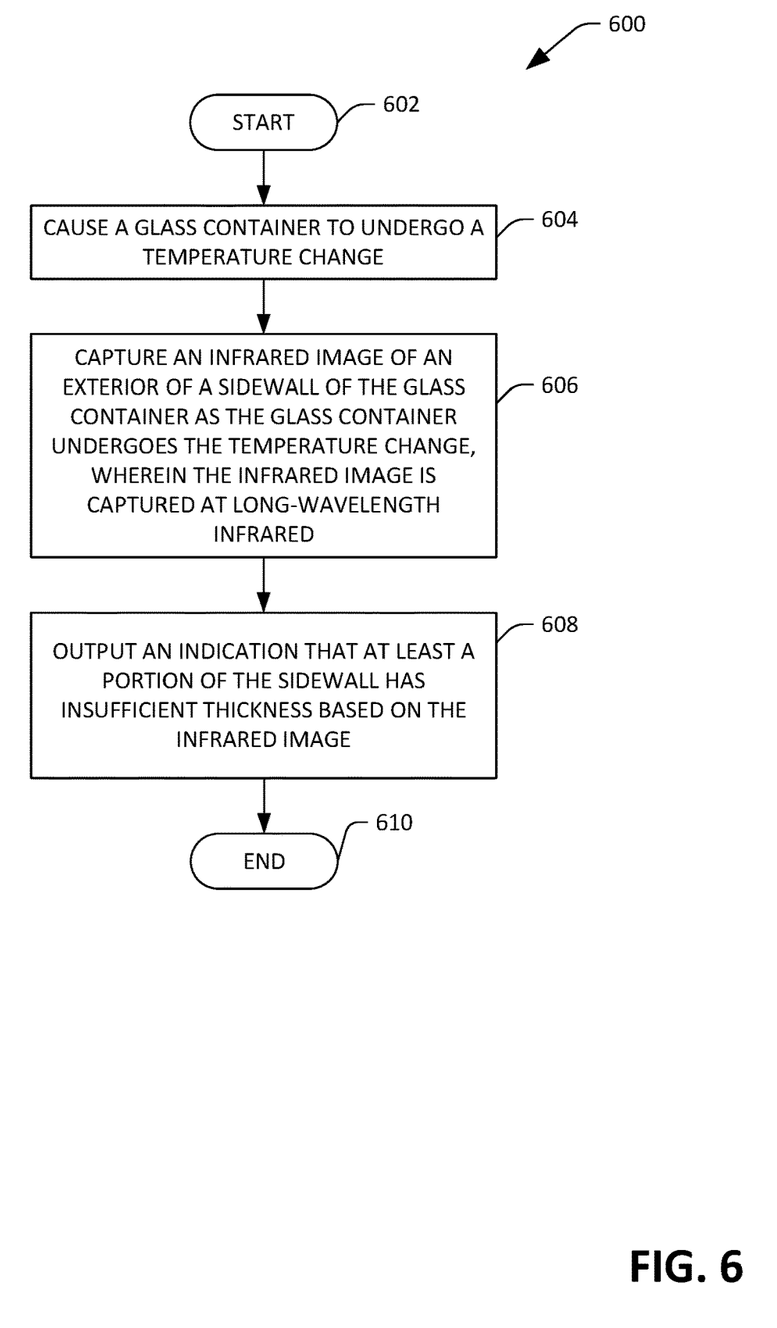
FIG. 6 is a flow diagram illustrating an exemplary methodology for determining whether a sidewall of a glass container has insufficient thickness based upon an infrared image of an exterior of the sidewall.
Figure 7:
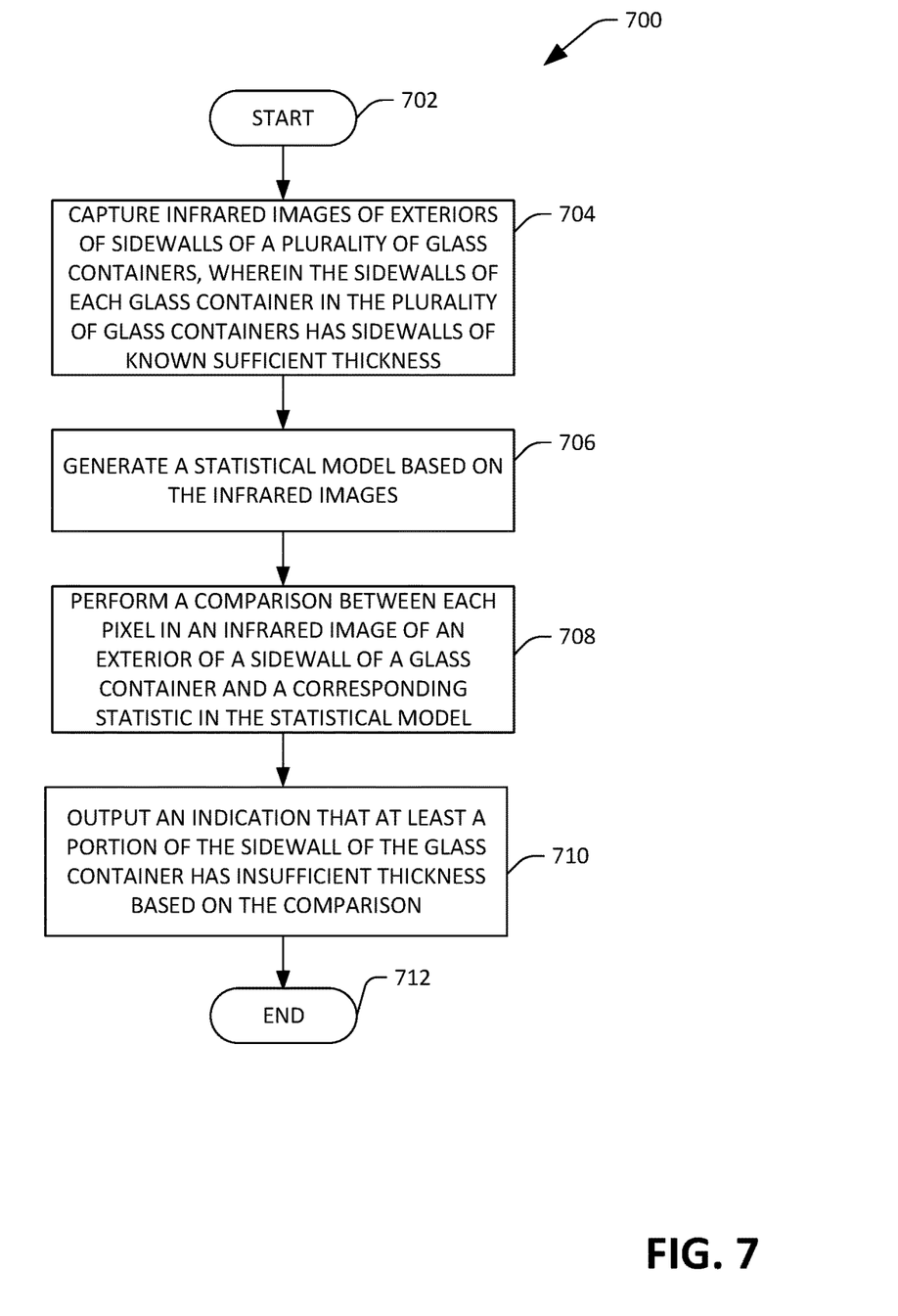
FIG. 7 is a flow diagram illustrating an exemplary methodology for determining whether a sidewall of a glass container has insufficient thickness using a statistical model.

FIGS. 6 and 7 depict exemplary methodologies pertaining to ascertaining whether any portion of a sidewall of a glass container has insufficient thickness. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processor and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Turning solely to FIG. 6, an exemplary methodology 600 for determining whether a sidewall of a glass container has insufficient thickness is illustrated. The methodology 600 begins at 602, and at 604 a heating or cooling means causes the glass container to undergo a temperature change. At 606, while the glass container undergoes the temperature change (e.g., while the glass container is being heated or cooled by the heating or cooling means or when the temperature of the glass container is moving to ambient temperature after being heated or cooled), an infrared camera captures an infrared image of an exterior of the sidewall of the glass container. The infrared camera is configured to capture the infrared image at mid to long-wavelength infrared. Each pixel in the infrared image is indicative of a temperature at a point on the exterior of the sidewall. At 608, a computing system in communication with the infrared camera receives the infrared image and outputs an indication that at least a portion of the sidewall has insufficient thickness based upon the infrared image. The methodology 600 concludes at 610.

With reference now to FIG. 7, an exemplary methodology 700 for determining whether a sidewall of a glass container has insufficient thickness using a statistical model is illustrated. The methodology 700 begins at 702, and at 704 infrared cameras capture infrared images of exteriors of sidewalls of a plurality of glass containers. Each glass container in the plurality of glass containers has sidewalls of known sufficient thickness. At 706, a computing system receives the infrared images and generates a statistical model based upon the images. The statistical model comprises statistics for each point on the exterior of the sidewall of an acceptable glass container. The statistics may be indicative of a thickness distribution at each point on the exterior of the sidewall. At 708, an infrared image of a sidewall of a container under inspection is captured, wherein the infrared image comprises pixels having respective values. At 710, the computing system outputs an indication that at least a portion of the sidewall of the glass container has insufficient thickness based upon the statistical model and the values of the pixels of the infrared image captured at 708. The methodology 700 concludes at 712.

Figure 8:
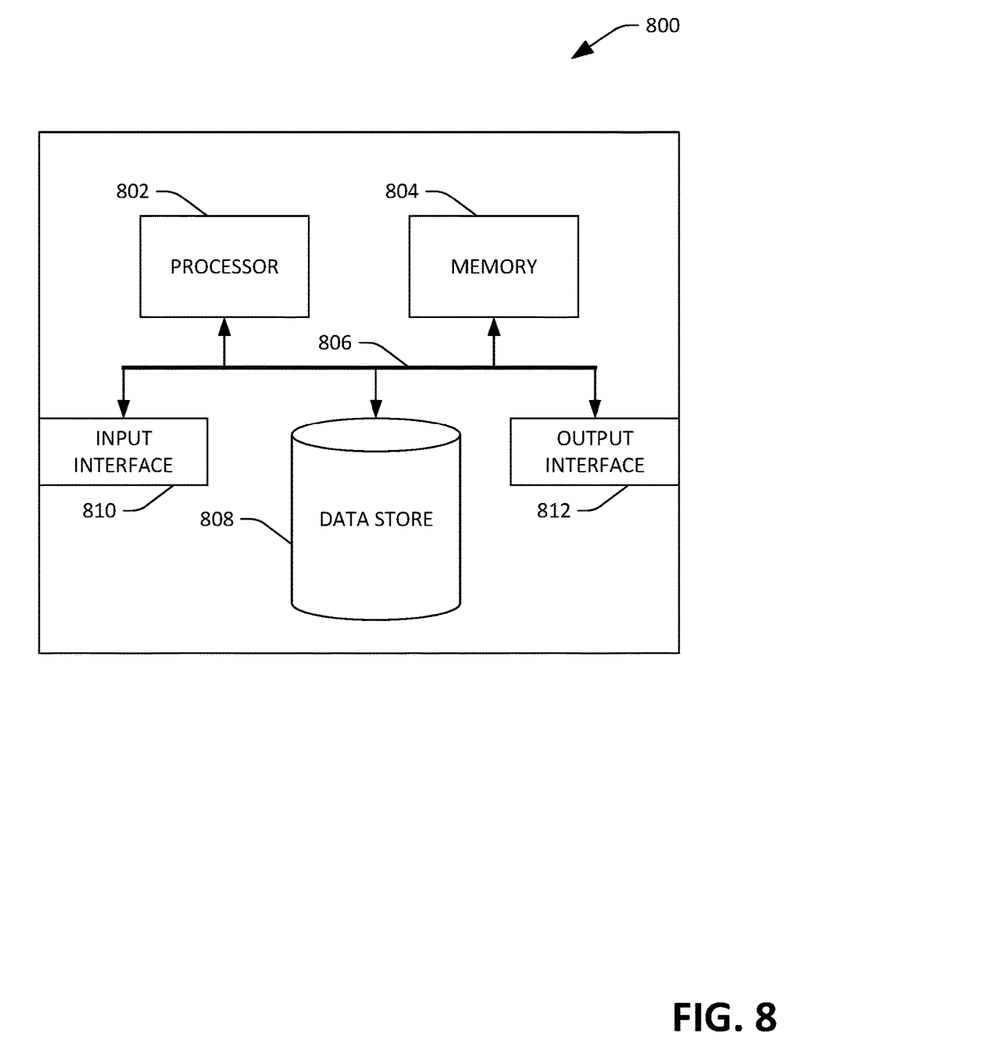
FIG. 8 is an exemplary computing device.

Referring now to FIG. 8, a high-level illustration of an exemplary computing device 800 that can be used in accordance with the systems and methodologies disclosed herein is illustrated. For instance, the computing device 800 may be used in a system that ascertains whether a sidewall of a glass container has insufficient thickness. By way of another example, the computing device 800 can be used in a system that generates a statistical model that can be used along with an infrared image to determine whether a sidewall of a glass container has insufficient thickness. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store infrared images, statistical models, etc.

The computing device 800 additionally includes a data store 808 that is accessible by the processor 802 by way of the system bus 806. The data store 808 may include executable instructions, infrared images, statistical models, etc. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that is configured to detect that a portion of a sidewall of a glass container has insufficient thickness, the system comprising:
    a heating or cooling source that is configured to alter a temperature of the portion of the sidewall of the glass container subsequent to the glass container exiting a hot end of a glass manufacturing system, wherein the heating or cooling source alters the temperature from a first temperature to a second temperature;
    an infrared camera that is configured to capture an infrared image of an exterior of the sidewall subsequent to the heating or cooling source altering the temperature from the first temperature to the second temperature and as the temperature of the portion of the sidewall is returning to the first temperature, wherein the infrared camera captures the infrared image based upon infrared radiation of wavelengths that are outside of a transmission window of glass that forms the sidewall of the glass container; and
    a computing system that is in communication with the infrared camera, the computing system configured to perform acts comprising:
        receiving the infrared image from the infrared camera; and
        outputting an indication that at least the portion of the sidewall of the glass container has insufficient thickness based upon the infrared image.

2. The system of claim 1, wherein the infrared image is representative of temperature distribution over the sidewall of the glass container.

3. The system of claim 1, wherein outputting the indication that at least the portion of the sidewall of the glass container has insufficient thickness comprises determining that the portion of the sidewall of the glass container has insufficient thickness based upon a statistical model of glass containers with acceptable thickness throughout their sidewalls.

4. The system of claim 1, wherein the infrared camera has a germanium lens.

5. The system of claim 1, wherein the computing system is configured to control the infrared camera to cause the infrared camera to capture the infrared image when the glass container enters an inspection region.

6. The system of claim 1, wherein the wavelengths are between 7 and 12 μm.

7. The system of claim 1, wherein the glass container is being transported on a conveyor when the infrared camera captures the infrared image.

8. The system of claim 7 further comprising:
    a removal mechanism in communication with the computing system, wherein the removal mechanism is configured to remove the glass container from the conveyor responsive to the computing system outputting the indication that at least the portion of the sidewall of the glass container has insufficient thickness.

9. The system of claim 1, wherein the heating or cooling source is configured to heat the glass container.

10. The system of claim 1, wherein the heating or cooling source is configured to cool the glass container.

11. The system of claim 1, wherein the infrared camera is configured to capture a second infrared image of the exterior of the sidewall subsequent to the heating or cooling source altering the temperature from the first temperature to the second temperature and as the temperature of the portion of the sidewall is returning to the first temperature, and further wherein computing system is configured to:

compare the infrared image with the second infrared image; and output the indication based upon the comparison between the infrared image and the second infrared image.

12. The system of claim 1 further comprising:

a sensor configured to output a signal to the computing system, wherein the computing system causes the infrared camera to capture the infrared image based upon the signal output by the sensor.

13. A method for detecting that a portion of a sidewall of a glass container has insufficient thickness, the method comprising:

altering a temperature of the portion of the sidewall of the glass container via a heating or cooling source subsequent to the glass container exiting a hot end of a glass manufacturing system, wherein the temperature is altered from a first temperature to a second temperature;

subsequent to the heating or cooling source altering the temperature from the first temperature to the second temperature and as the temperature of the portion of the sidewall is returning to the first temperature, generating an infrared image of an exterior of the sidewall of the glass container, wherein the infrared image is indicative of temperatures across the exterior of the sidewall of the glass container; and outputting an indication that the portion of the sidewall of the glass container has insufficient thickness based upon the infrared image.

14. The method of claim 13, wherein altering the temperature of the portion of the sidewall comprises at least one of applying heat to the glass container or removing heat from the glass container.

15. The method of claim 13 further comprising:

repeating the acts of altering, generating, and outputting for each glass container being transported on a conveyor.

16. The method of claim 13, further comprising:

simultaneously generating a plurality of other infrared images of the exterior of the sidewall of the glass container with the infrared image;

generating an image that is representative of an entirety of the exterior of the sidewall of the glass container based upon the infrared image and the plurality of other infrared images; and outputting the indication that the portion of the sidewall of the glass container has insufficient thickness based upon the generated image.

17. The method of claim 13, wherein the infrared image is generated by an infrared camera having a germanium lens.

18. The method of claim 13, wherein the glass container is asymmetric.

19. The method of claim 13, wherein the glass container is being transported by a conveyor when the infrared image is generated, the method further comprising causing the glass container to be removed from the container responsive to outputting the indication that the portion of the sidewall of the glass container has insufficient thickness.

20. A glass container inspection system that is configured to detect that a portion of a sidewall of a glass container has insufficient thickness, the glass container inspection system comprising:

means for altering a temperature of the portion of the sidewall of the glass container subsequent to the glass container exiting a hot end of a glass manufacturing system, wherein the temperature is altered from a first temperature to a second temperature;

means for generating an infrared image of an exterior of a sidewall of the glass container subsequent to the means for altering the temperature from the first temperature to the second temperature and as the temperature of the portion of the sidewall is returning to the first temperature, wherein the means for generating the infrared image detects infrared light having wavelengths between 7 and 12 μm; and a computing system that is configured to receive the infrared image and output an indication that the portion of the sidewall of the glass container has insufficient thickness based upon the infrared image.

* * * * *